United States Patent [19]

Roshdy et al.

[11] Patent Number: 4,946,043
[45] Date of Patent: Aug. 7, 1990

[54] RETAINER FOR SURGICAL SUTURES

[75] Inventors: Constance E. Roshdy, North Brunswick, N.J.; Robert J. Cerwin, Pipersville, Pa.; Marvin Alpern, Glen Ridge, N.J.

[73] Assignee: Ethicon, Inc., Somerville, N.J.

[21] Appl. No.: 446,226

[22] Filed: Dec. 4, 1989

Related U.S. Application Data

[62] Division of Ser. No. 346,421, May 3, 1989, Pat. No. 4,887,710, which is a division of Ser. No. 264,292, Oct. 28, 1988, Pat. No. 4,884,681.

[51] Int. Cl.$^5$ .............................................. A61L 15/00
[52] U.S. Cl. ..................................................... 206/63.3
[58] Field of Search ..................... 206/63.3, 491, 492, 206/353; 229/DIG. 4

[56] References Cited

U.S. PATENT DOCUMENTS

| | | | |
|---|---|---|---|
| D. 272,600 | 2/1984 | Kubas | 206/63.3 |
| 3,939,969 | 2/1976 | Miller et al. | 206/63.3 |
| 4,089,409 | 5/1978 | Cerwin | 206/63.3 |
| 4,120,395 | 10/1978 | Mandel et al. | 206/523 |
| 4,249,656 | 2/1981 | Cerwin et al. | 206/63.3 |
| 4,253,563 | 3/1981 | Komarnycky | 206/63.3 |
| 4,406,363 | 9/1983 | Aday | 206/63.3 |
| 4,413,727 | 11/1983 | Cerwin et al. | 206/63.3 |
| 4,427,109 | 1/1984 | Roshdy | 206/63.3 |
| 4,483,437 | 11/1984 | Cerwin et al. | 206/63.3 |
| 4,533,041 | 8/1985 | Aday et al. | 206/63.3 |
| 4,555,016 | 11/1985 | Aday et al. | 206/63.3 |
| 4,572,363 | 2/1986 | Alpern | 206/63.3 |
| 4,574,957 | 3/1986 | Stead | 206/63.3 |
| 4,615,435 | 10/1986 | Alpern et al. | 206/63.3 |

Primary Examiner—William Price

[57] ABSTRACT

An improved retainer for surgical sutures is provided which includes a suture retaining compartment comprising a suture winding panel with the panel having a pair of holding panels foldably connected to longitudinal edges of the suture winding panel. The holding panels are foldably connected to the winding panel by at least three gussets formed at the edges of the suture winding panel. The gussets at the ends of the foldable connection prevent frictional compression of the wound suture at the corners of the retaining compartment, and the central gussets or gussets engender a convex curvature to the holding panels, thereby creating a low friction volumetric compartment which retains the suture in place. The suture retainer also includes a needle holding means mounted at the intended location of the needle. In illustrated embodiments of the present invention the holding means is angularly disposed with respect to the longitudinal dimension of the retainer to afford ease of needle withdrawal, and in some embodiments the holding means is located on a foldable needle park panel. In some embodiments the retainer includes an insert against which the suture is wound. This insert provides several features, including preventing snagging of the suture on the needle holding means during suture withdrawal, and protection of the needle point. The insert may also include a flap to prevent the suture from snagging on a corner of the insert during withdrawal.

7 Claims, 8 Drawing Sheets

FIG-1
FIG-1a
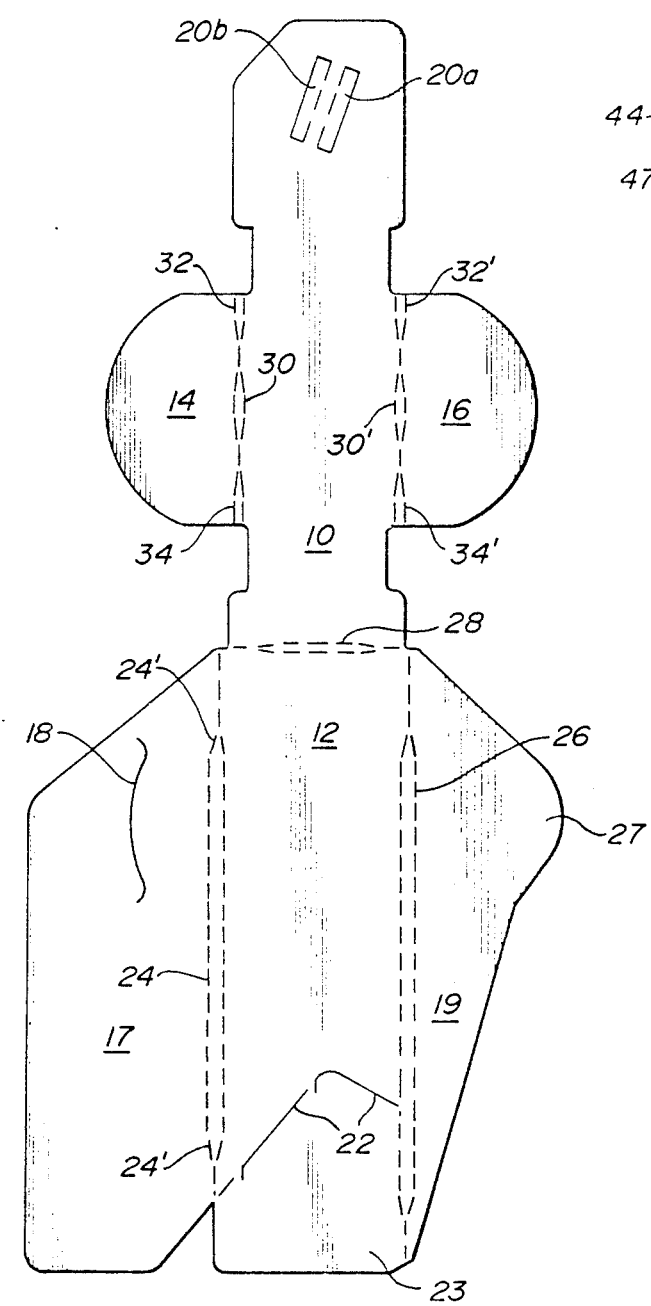
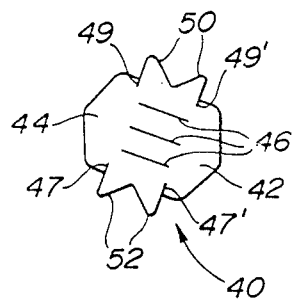

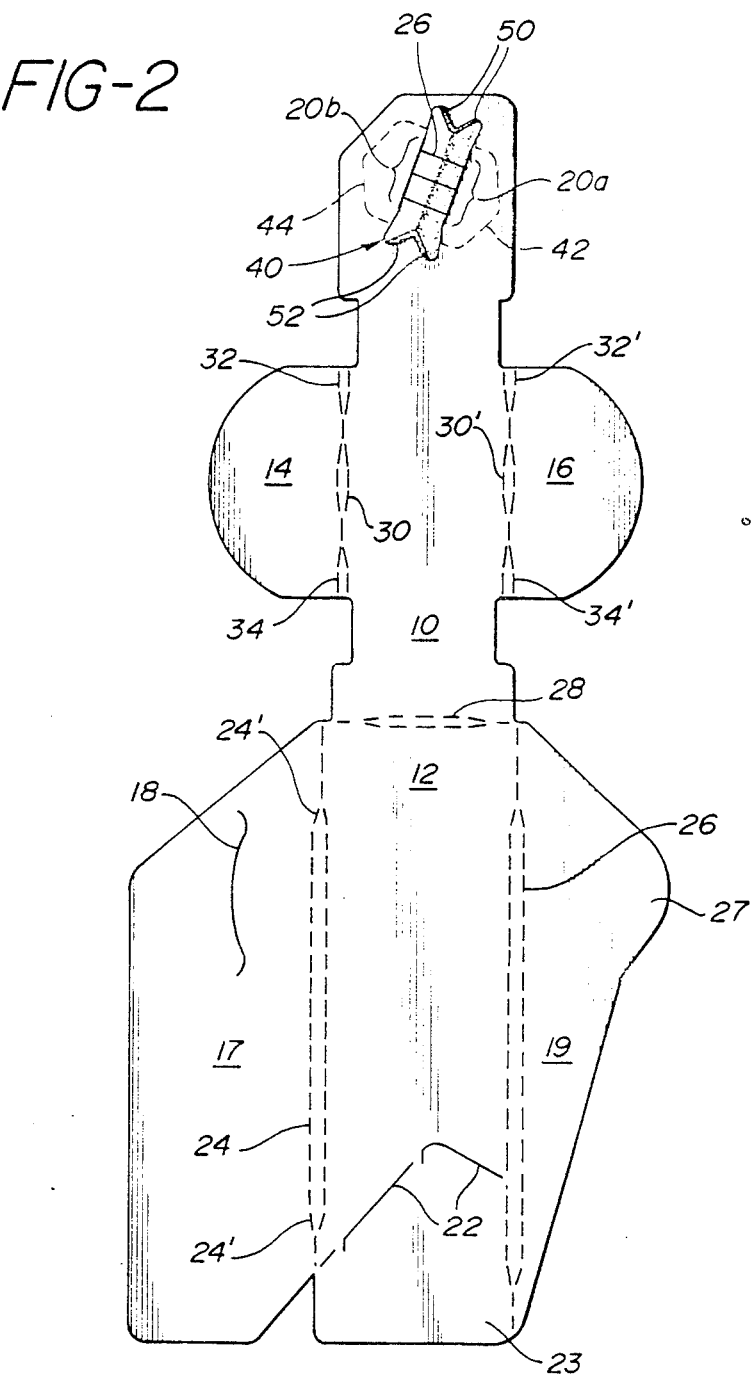

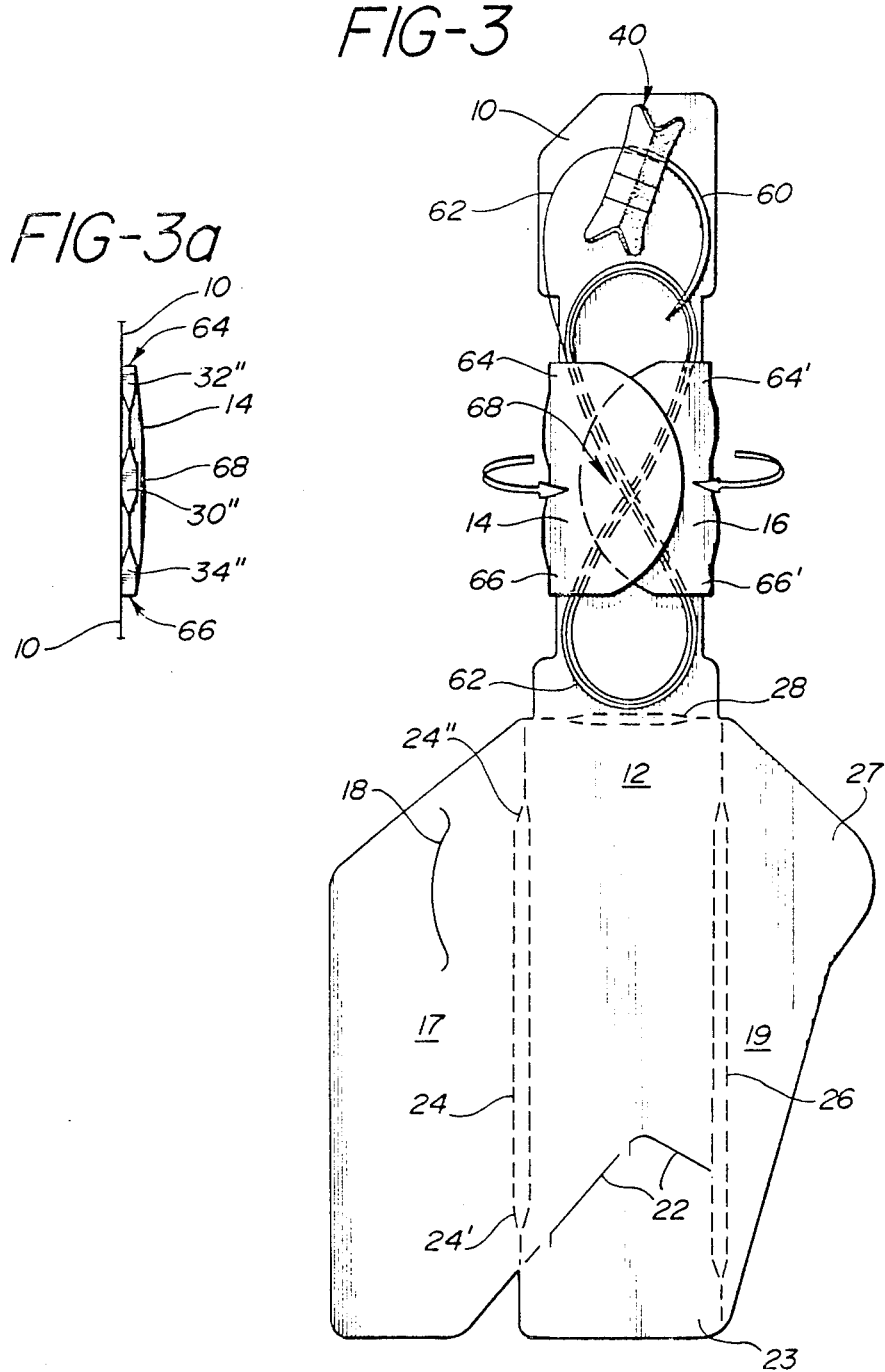

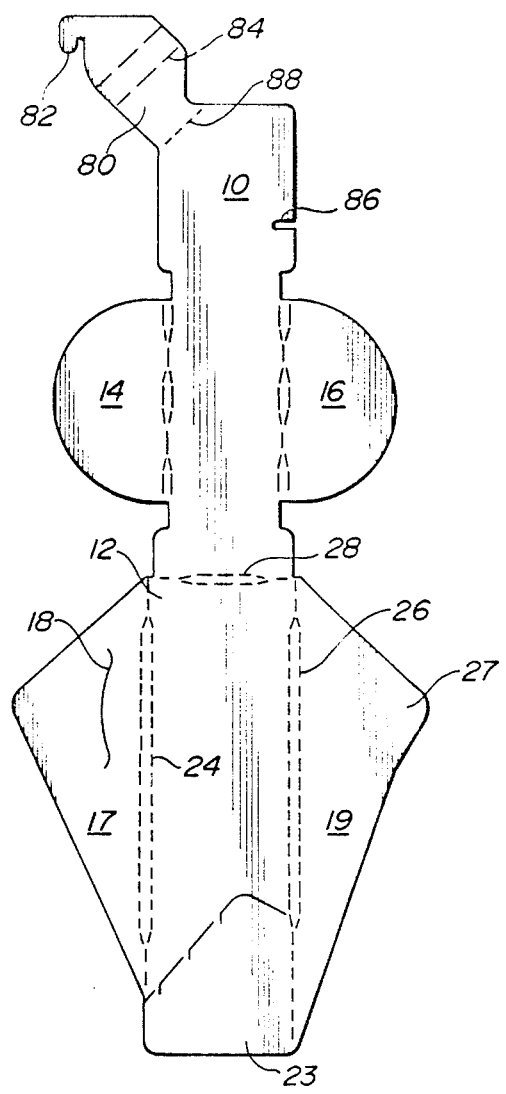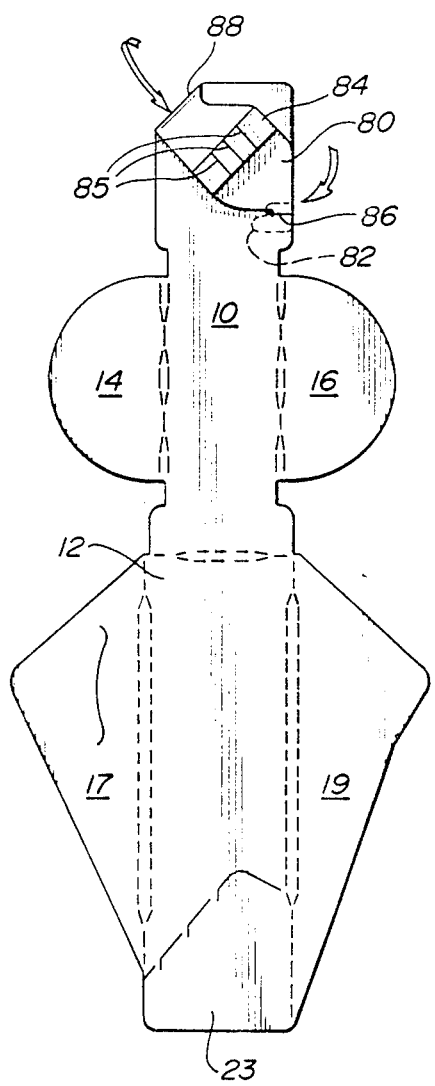

4,946,043

RETAINER FOR SURGICAL SUTURES

This is a division, of application Ser. No. 346,421, filed May 3, 1989, now U.S. Pat. No. 4,887,710, which is a division of application Ser. No. 264,292, filed Oct. 28, 1988, now U.S. Pat. No. 4,884,681.

The present invention relates to a retainer for surgical sutures and more particularly to a multiple panel retainer for securely holding surgical sutures.

Packages for surgical sutures are constructed according to the nature of the suture and its intended use. The packages are designed taking into consideration the economics of the package and the method of placing the sutures in the package. In general, the ideal package protects the suture during handling and storage yet allows the suture to be removed with the minimum of difficulty and the package itself should be economical to produce.

The more popular suture packages consist of a folded paper retainer with a suture therein and with the retainer contained in a sterile hermetically sealed envelope. In many instances, the sterility of the suture in the envelope is maintained by a second sealed outer wrap. When the suture is to be used, the outer wrap is opened in the operating room and the sealed envelope deposited in the sterile area. Sterile personnel thereupon tear open the sterile envelope to gain access to the suture.

Many packages have been developed to provide: easy access to the sutures, simplified winding of the suture, dispensing of a single suture from a package containing multiple sutures, and the like. Representative packages are more fully described in U.S. Pat. Nos. 3,936,696, 3,280,971, 3,490,192, 4,089,409, 4,126,221, 4,253,563, 4,249,656, 4,491,218, 4,483,437, 4,413,727, 4,412,614, 3,985,227, and 4,120,395. As mentioned above, packages for surgical sutures are often constructed according to the nature of the suture being packaged. For example, if the suture is made from material that is heat sensitive it is important that the package totally enclose the suture to protect it from heat during sterilization or storage of the suture. If the suture is made from a monofilament material; i.e., a material which tends to take a set in a configuration which is held for any period of time, the package should be designed to take that property into consideration. Also, suture packages should be designed for efficiency in use; i.e., when the nurse is opening a suture package in the surgical environment, the nurse should have control of the opening of the package and the package should not open prematurely or unwarrantedly. It is desirable that the package be easily opened and in many instances opened using one hand, i.e. the package held in the hand and readily opened by a finger because the other hand of the person who desires to open the package may be occupied.

U.S. Pat. No. 4,615,435, entitled "RETAINER FOR SURGICAL SUTURES" and issued in the names of the present inventors describes a suture package which is simple, economical and effective for its intended purpose. The package described in this patent includes a suture winding panel against which a suture is wound. The wound suture is retained in place by two foldable suture holding panels. A suture enclosing panel, attached to the winding panel, is folded over the holding panels and retainer interlocking panels are then folded around the winding panel and interlocked to close the package. The package also includes needle holding means for retaining the needle or needles of an armed suture.

The present inventors have found that the package described in this patent may create undesirable friction when the suture is withdrawn from the package. Specifically, they have found that it is desirable for the suture winding panel and overlapping holding panels to exert only minimal compressive forces when retaining the suture in the package. It would be desirable to reduce these compressive forces by retaining the suture in a compartment within the package rather than compressing it between the winding panel and the holding panels.

The needle holding means shown in the aforementioned U.S. patent comprises an adhesively attached strip of foam. The present inventors have found it desirable under some circumstances to employ needle holding means which do not employ an adhesive. Such a needle holding means should be simple to employ during manufacture of the suture package, and should be oriented for ease of withdrawal of the needle and suture from the package.

The present inventors have also found that it is possible during withdrawal of the suture for the suture to catch or snag on the needle holding means at the end of the winding panel. It would be desirable to employ means to prevent suture snagging on the holding means during withdrawal of the suture.

When the needle is parked in the needle holding means, it is often the case that the point of the needle is exposed, or that the needle point is exposed immediately upon opening the package. Since exposure of a needle point can expose hospital personnel to accidental needle sticks, it is desirable for the needle point to be protected in the package until the time that the needle is grasped and withdrawn from the package.

The present invention provides an improved retainer for surgical sutures. The retainer includes a suture retaining compartment comprising a suture winding panel with the panel having a pair of holding panels foldably connected to longitudinal edges of the suture winding panel. The holding panels are foldably connected to the winding panel by at least three gussets formed at the edges of the suture winding panel. The gussets at the ends of the foldable connection prevent frictional compression of the wound suture at the corners of the retaining compartment, and the central gussets or gussets engender a convex curvature to the holding panels, thereby creating a low friction volumetric compartment which retains the suture in place. The suture retainer also includes a needle holding means mounted at the intended location of the needle. In illustrated embodiments of the present invention the holding means is angularly disposed with respect to the longitudinal dimension of the retainer to afford ease of needle withdrawal, and in some embodiments the holding means is located on a foldable needle park panel. In some embodiments the retainer includes an insert against which the suture is wound. This insert provides several features, including preventing snagging of the suture on the needle holding means during suture withdrawal, and protection of the needle point. The insert may also include a flap to prevent the suture from snagging on a corner of the insert during withdrawal. In the drawings:

FIG. 1 is a plan view of one embodiment of the improved retainer of the present invention;

FIG. 1a is a plan view of a foam needle holder suitable for use with the retainer of FIG. 1;

FIG. 2 is a plan view of the improved retainer of FIG. 1 showing the needle holder of FIG. 1a inserted in place;

FIGS. 3 and 3a illustrate the suture retaining compartment formed by folding the suture holding panels over the suture winding panel;

Figure 4:
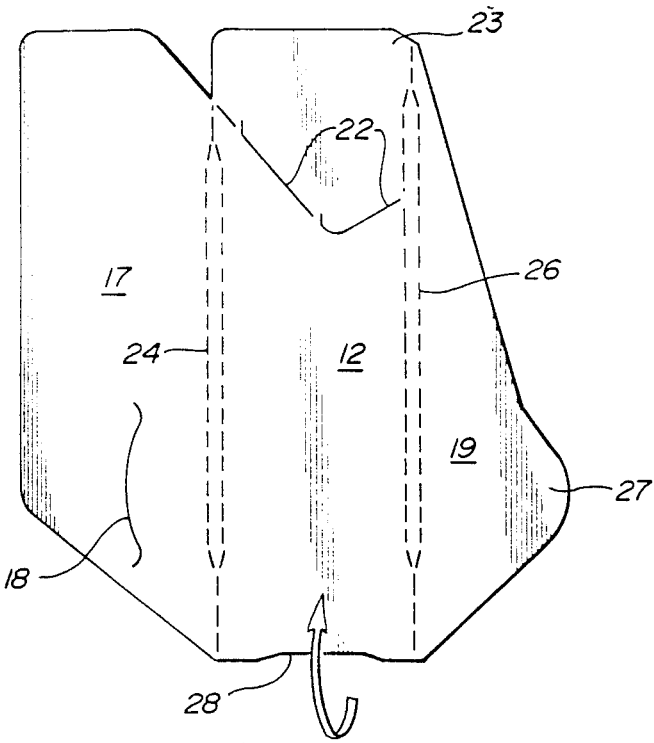
FIGS. 4-6 illustrate the assembly and use of the retainer of FIGS. 1-3.

FIGS. 7a, 7b, 8 and 9 illustrate use of the retainer of the present invention with a suture winding insert; and FIG. 10a-10c and 11a-11c illustrate further embodiments of the present invention in which the needle holder is separately located on a needle park panel disposed for angular disposition of the needle holder with respect to the longitudinal dimension of the retainer. The drawings illustrate the various stages in preparing and folding embodiments of the retainer of the present invention. Similar features of the retainer are designated by the same reference numerals throughout the drawings. The term "suture" when used in this application relates to both a needle or unneedled strand of suture material.

In FIG. 1 there is depicted an unfolded suture retainer of the present invention. The retainer comprises a suture winding panel 10 which is generally rectangular in shape and has a pair of longitudinal side edges demarcated by gussets 30, 32, 34 and 30', 32', and 34' and a pair transverse ends, the lower one of which is demarcated by a gusset 28. Foldably connected to each side edge is a semicircular shaped suture holding panel 14 and 16. The straight side of the semicircular suture holding panel is foldably connected to the longitudinal edge of the suture winding panel. Adjacent to the upper transverse end of the suture winding panel are slots 20a and 20b for insertion of a foam member 40, shown in FIG. 1a. This member holds needles attached to the suture. Foldably connected to the opposite transverse end of the suture winding panel at gusset 28 is the suture enclosing panel 12. This panel is rectangular in shape and is substantially coextensive with the suture winding panel when folded. This suture enclosing panel has a pair of longitudinal sides edges demarcated by gussets 24 and 26 and a pair of transverse ends at gusset 28 and at the bottom of the package. A slit 22 in the suture enclosing panel forms a tear flap 23 in the retainer for opening the package as described below. Foldably connected to each longitudinal side edge of the suture enclosing panel is a retainer interlocking panel 17 and 19. The retainer interlocking panels are irregular in shape with the long side of the panels foldably connected to the longitudinal edge of the suture enclosing panel. One of the retainer interlocking panels has a slit 18 which is used to interlock with the free end 27 of the opposite interlocking retainer panel as will be hereinafter described.

Referring to FIG. 1a, the foam needle holding member 40 is shown. The member 40 is approximately one-sixteenth of an inch thick and is symmetrically shaped for nonpreferential insertion into the slots 20a and 20b of the retainer. Disposed on either side of the central portion of the member 40 are a pair of insertion tabs 42 and 44. Four small slits 47, 49 and 47', 49' are cut in the member 40 at the jointure of the insertion tabs and the central portion of the member 40. The dimension between each pair of slits is approximately equal to the length of the slots 20a and 20b, so that the longitudinal ends of the insertion tabs will extend beyond the ends of the slots 20a and 20b, thereby retaining the member 40 securely within the slots. The central portion of the member 40 is scored with a number of needle retaining slits 46 in which needles may be securely held in place. Extending from the longitudinal ends of the central portion of the member 40 are ears 50 and 52, which extend beyond the slots 20a and 20b when the member 40 is inserted in the retainer. The v-shape formed at the jointure of each pair of ears is located at the center of the member 40 so that the member will preferentially fold at its center along the apexes of the v-shapes.

The foam needle holding member 40 is shown inserted in place in the retainer slots 20a and 20b in FIG. 2. As indicated by the brackets, the ears 50, 52 extend beyond the longitudinal ends of the slots. The slots are spaced apart by a dimension which is less than the width of the unfolded central portion of the member 40. Thus, in order to insert the member 40 in the slots 20a and 20b, it must first be folded down its center. The member 40 thus sits in an inverted v-shape after insertion. This causes the needle retaining slits 46 to be in an upwardly extending v-shape, enabling the member 40 to hold needles of various gauges. Also, the inverted v-shape causes compression longitudinally along the member 40. This compression tends to force the slits 46 closed and maintains compressive forces which will hold needles securely in place.

Figure 8:
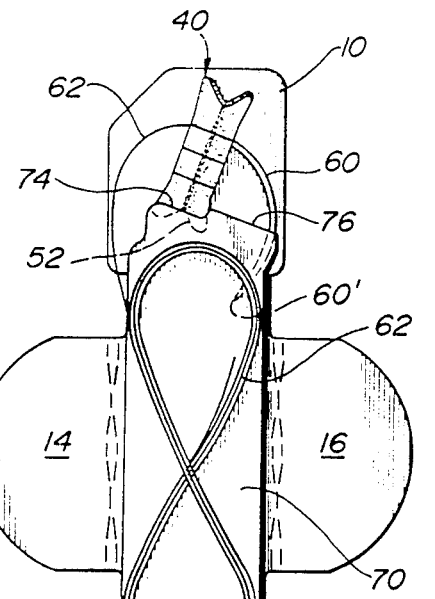

The suture retainer is assembled by winding a suture 62 in a figure-8 pattern against the suture winding panel 10, as described in the aforementioned U.S. Pat. No. 4,615,435, and placing the needle 60 of the suture in the member 40. The suture holding panels 14 and 16 are then folded over the suture winding panel to enclose the suture 62 in a suture retaining compartment formed between the winding and holding panels, as shown in FIG. 3. Rather than compressing the suture between the panels, the retaining compartment exhibits a thickness dimension which prevents the suture from being pinched or frictionally held in place. The retaining compartment is formed by operation of the gussets at the longitudinal edges of the suture winding panel, as explained by concurrently referring to FIG. 3a.

It may be seen in FIG. 3 that the wound suture extends from the top and bottom of the retaining compartment at the corners 64, 66, 64' and 66' of the compartment. If the fold line employed at these corner regions is only a single fold line as shown in our aforementioned U.S. patent, the suture will be pinched at these corner regions, creating frictional forces as the suture is withdrawn from the retainer. To prevent the occurrence of pinching at the corners, gussets 32, 34, 32' and 34' are formed at these corners. These gussets comprise two parallel score marks at the corners which taper together to a single score mark toward the center of the fold. Thus, the suture 62 is not pinched at these corners, but is loosely held in the volumetric spaces at each of the corners.

When these pairs of gussets are each connected by a single central fold line, the tapering of the gussets to the single central fold line between them will impart a concave curvature to the suture holding panels 14 and 16. The curvature will thereby apply compressive forces at the center of the suture wind, where the centers of the holding panels compress the suture against the suture winding panel. The compressive forces will thereby securely compress the wound suture in place in the compartment. However, in a preferred embodiment of the present invention, it is preferable to hold the wound suture loosely in place in the center of the compartment also. Accordingly, a gusset 30, 30' is formed between each pair of end gussets. The gussets 30, 30' comprise central parallel scored lines which taper to a single line as they approach each end gusset. In contrast to a single fold line, the central gussets 30, 30' impart a convex curvature to the suture holding panels, thereby defining a central volumetric space between the holding panels and the suture winding panel. Thus, the suture 62 is held loosely in the center of the compartment. The enclosed suture may be withdrawn from the compartment with no significant frictional resistance.

FIG. 2 shows only a single gusset 30' formed between the end gussets 32' and 34'. It may be appreciated that a number of gussets can be employed between the end gussets, providing a flatter, less convex curvature to the suture holding panels.

In a preferred embodiment the fold lines between the suture winding panel 10 and the suture enclosing panel 12, and the fold lines between the suture enclosing panel and the interlocking retainer panels 17 and 19 are dual fold lines to provide gussets 28, 24, and 26 between the enclosing panel and the suture winding and retainer panels. These gussets prevent undue pressure from being placed on the suture in the retainer and allow the suture to be readily removed from the retainer and not held therein by excess friction. It should be noted that volumetric folds could be provided simply by employing two parallel score lines over the lengths of each of these folds. However, such dual lines do not promote a preferential folding axis along the fold. Rather, the folding panels can tend to fold along one line at one end of the panel and along the other line at the other end of the panel. The result will be a cocking of the panel and an angular bend instead of a uniform, box-like fold. This cocking problem is eliminated by tapering each of the parallel score lines to a single score line, as indicated at 24' at the ends of parallel lines 24. When the panel 17 is folded, the gusset will then preferentially fold along each of the single score lines at the ends of the gusset, and the gusset itself will fold evenly along both parallel lines. In the retainer shown in U.S. Pat. No. 4,615,435 preferential folding would not occur at the bottoms of gussets 20 and 21, as these gussets continue as parallel score lines to the end of the fold.

It may be appreciated that preferential folding will occur in accordance with the same principle at the triple gusset folds joining the holding panels 14 and 16 to the suture winding panel 10. This is because of the single score lines separating each of the gussets 30–32; 30–34; 30'–32'; and 30'–34'.

Once the suture has been wound as described in U.S. Pat. No. 4,615,435, the two suture holding panels are folded on top of the wound suture as shown in FIG. 3. Once the suture holding panels are folded over the suture to hold the suture in place the retainer may be removed from the winding pins. As is shown in FIG. 4, the suture enclosing panel 12 is then folded on top of the suture holding panels. The pair of interlocking retainer panels are folded behind the suture winding panel and interlocked by placing the free end 27 of one of the interlocking retainer panels 19 in the slit 18 of the other interlocking retainer panel as shown in FIG. 5.

Referring to FIGS. 1 and 4, adjacent the ends of the interlocking retainer panels closest to the free end of the suture enclosing panel there is a scored area 22 extending transversely of the suture enclosing panel. The purpose of this scored portion will be hereinafter described. The package shown in FIG. 5 totally encloses and protects the suture and the needle, yet it is a simple matter to hold the package in one hand, grasp the edge of tear flap 23 at the corner of the package, and tear the flap 23 downward along the scored area 22 as shown in FIG. 6, thereby revealing the enclosed needle and suture. This allows ready and simple one handed access to the suture in the package and the needle 60 may then be grasped with a forceps and pulled from the package with its trailing suture. In the embodiment of FIG. 6, the needle 60 is grasped with a forceps held in the right hand with the point of the needle oriented on the thumb side of the forceps. It may be appreciated that a similar package may be made for left-handed withdrawal by forming the package in mirror image fashion.

Figure 5:
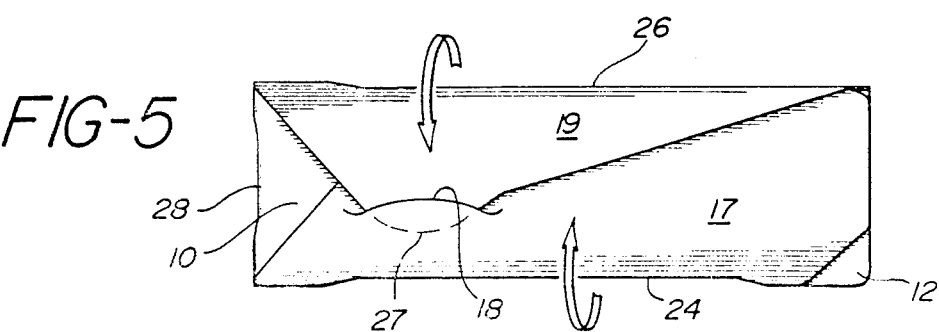
Figure 6:
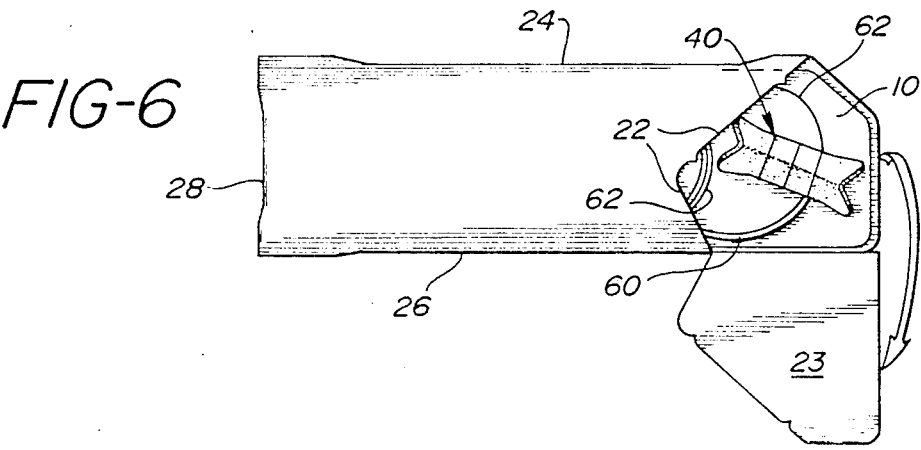

The folded retainer shown in FIG. 5 with the suture therein may then be wrapped in a suitable foil-film overwrap as is well known in the art and sterilized by any of the techniques well known in the art depending on the type of suture material used. As can be appreciated, this is a simple and economical package to produce.

Figure 7A:
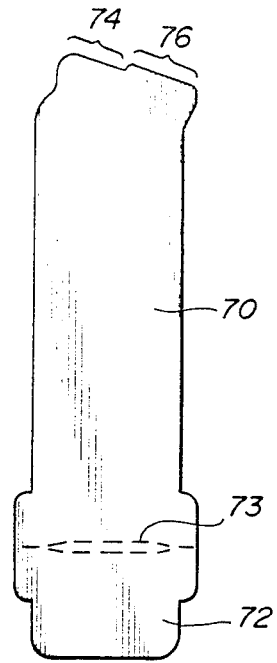
Figure 7B:
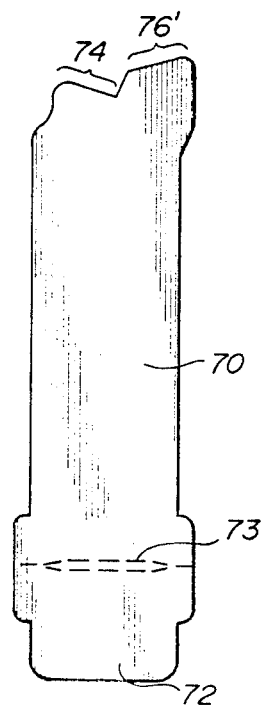

It may be desirable to provide the retainer of FIGS. 1-6 with an insert against which the suture is wound as shown in FIG. 7a, 7b, and 8. The insert 70 there shown provides several features in the retainer. Referring first to FIG. 7a, the insert 70 is seen to have two longitudinal edges and two transverse ends. At the upper transverse end is a foam member protecting edge 74 and a needle point protecting edge 76. At the lower transverse end is a flap 72 delineated from the upper portion of the insert by a gusset 73. The insert 70 of FIG. 7a is designed for use in the retainer package of FIGS. 1-6 with large gauge suture needles. FIG. 7b shows another embodiment of an insert with an extended needle point protecting edge 76'. The embodiment of FIG. 7b is designed for use with small gauge suture needles.

Referring to FIG. 8, use of the insert 70 is shown in the suture retainer of FIG. 1. The insert 70 is placed against the suture winding panel 10 with the gusset 73 aligned with the gusset 28 of the package. When so positioned, the foam member protecting edge 74 is located on top of the foam needle park 40 with the insert covering the lower ears 52 of the park. The needle 60 is placed in the foam needle park 40 with the point of the needle lodged behind the insert at the needle point protecting edge 76. The suture 62 is then wound against the insert 70 as described above. When the suture enclosing panel 12 is folded upward as shown in FIG. 4, the package will fold at its gusset 28 and the insert will simultaneously fold at its gusset 73, bringing the flap 72 upward and on top of the lower loops of the suture 62.

Figure 9:
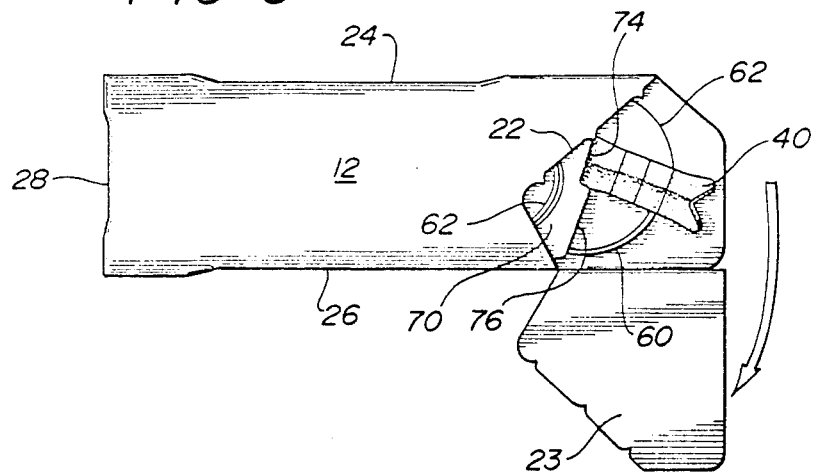

Referring now to FIG. 9, the assembled retainer of FIG. 8 is shown after the tear flap 23 is pulled downward to open the package. It may be seen that there is no danger of inadvertent needle sticks during the opening of the package, as the needle point is protected behind the edge 76 of the insert. The points of smaller gauge needles would be similarly protected behind the extended edge 76' of the small needle insert of FIG. 7b. The insert also protects the suture material from damage by the needle, as the suture is located on top of the insert while the needle is located behind the insert. As the suture is withdrawn from the retainer, the loops of suture material will slide out smoothly over the foam member 40. Without the insert it is possible for the loops of suture to snag on the lower ears 52 of the foam member as they are withdrawn. This problem is eliminated when these lower ears are covered by the insert at its edge 74, and the insert further functions to flatten down the lower end of the needle park for smooth suture withdrawal. It was also found that if the insert is terminated at the location of the gusset 73, the lower loops of the suture could catch and snag on the lower corners of the insert. This problem is prevented by the flap 72, which eliminates the lower corners at the bottom of the suture loops. The wound suture will thus pull smoothly from the retainer in FIG. 9 without snagging by reason of these features of the insert 70.

It may be seen in the previous embodiments of the present invention that the foam member 40 is oriented at approximately a 20° angle with respect to the longitudinal axis of the package. As FIGS. 6 and 9 illustrate, this orientation of the needle park locates the needle 60 so that the user can see the barrel of the needle where the suture is attached on one side of the needle park, and the major length of the needle on the other side. The user can then grasp the needle with a forceps as described above in the preferred location, slightly forward of the needle barrel, with the point located on the thumb side of the forceps. The 20° orientation has been found to be suitable for the large gauge needle shown in these embodiments. For smaller gauge needles a greater angle with respect to the longitudinal axis of the package would be employed, and also depending upon the curvature of the needle (e.g., ⅜ round, ½ round, ⅝ round, etc.) It has been found that a preferred range of angles for the needle park is a range of 10° to 60°, depending upon these factors.

Figure 10C:
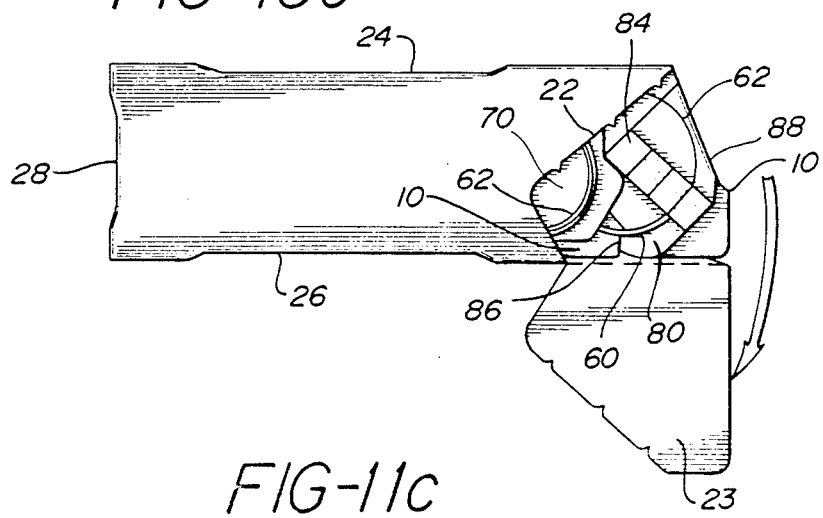

Another technique for locating the foam member 40 in the desired location is to provide a foldable needle park panel as shown in FIGS. 10a-10c. Referring to FIG. 10a, a retainer constructed as previously described is shown with a needle park panel 80 attached to the upper left corner of the suture winding panel 10. The needle park panel 80 is foldably attached to the winding panel by a score line 88. At the upper corner of the needle park panel 80 is a locking tab 82. On the reverse side of the panel 80 is an adhesively attached foam needle park 84. Located in the right longitudinal edge of the winding panel 10 is a locking tab notch 86 for engaging the locking tab 82.

The needle park is located in its desired position on the winding panel 10 by folding the needle park panel downward over the winding panel as shown in FIG. 10b. This is preferably done after scoring the needle park 84 with needle slits 85, before the needle park panel is folded over the winding panel. The locking tab 82 is snapped through the notch 86 to a position behind the winding panel to hold the needle park in place.

The package of FIGS. 10a and 10b is shown fully assembled in FIG. 10c. It may be seen that the tear tab 23 is grasped at the edge of the package above the score line 88 to tear the flap 23 downward when opening the retainer package. It is also seen that the loop of suture 62 is inside of the outwardly located needle 60 in this embodiment.

It may be appreciated that the needle park panel 80 may be provided with slots similar to slots 20a and 20b of FIG. 1 for use of the package with an inserted foam member 40 in place of the adhesively attached foam member 84.

Figure 11C:
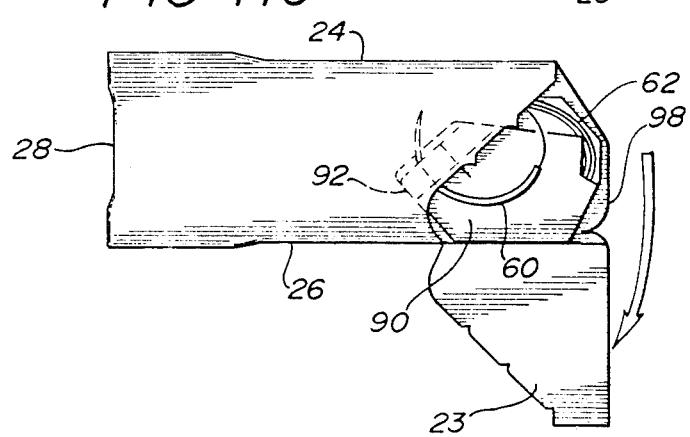
Figure 11A:
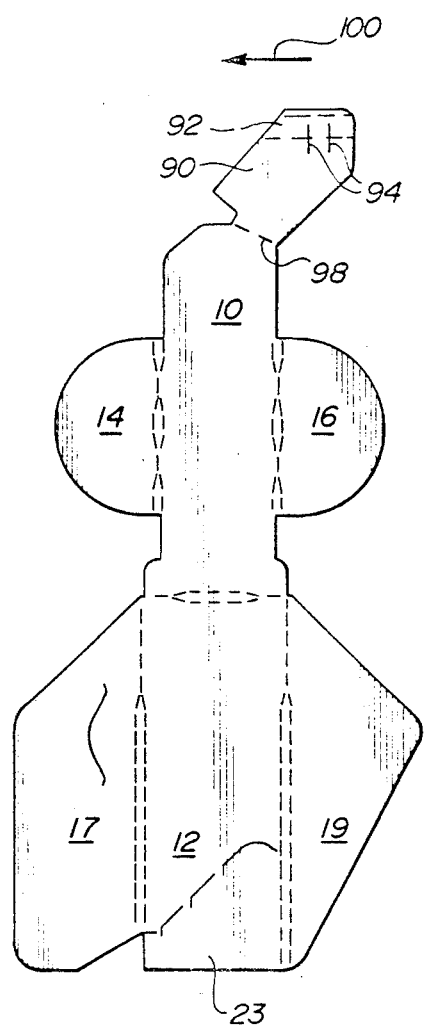
Figure 11B:
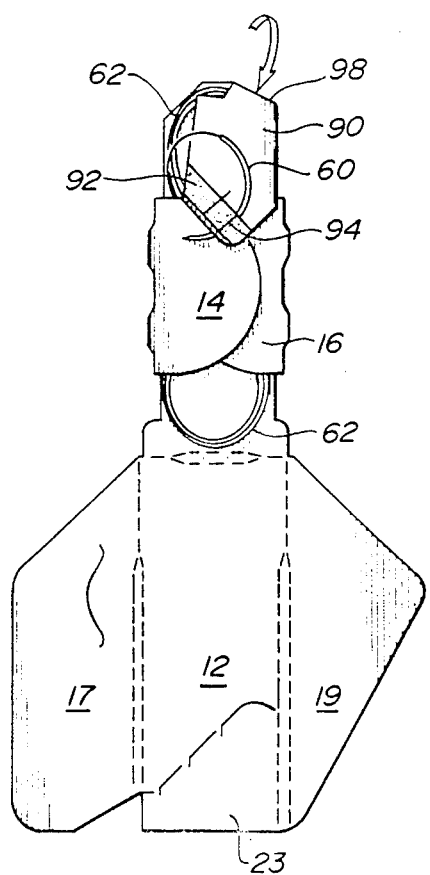

Another embodiment of a retainer package with a needle park panel is shown in FIGS. 11a-11c. In this embodiment the needle park panel 90 is located at the upper right hand corner of the suture winding panel 10. An adhesively attached foam needle park 92 is affixed to the back surface of the panel 90 and is scored with needle slits 94. The needle park panel 90 is folded over the winding panel 10 at a scored line 98.

The embodiment of FIG. 11a provides an advantage in manufacture of the retainer package in that the adhesive strip 92 is affixed orthogonal to the longitudinal axis of the package and parallel to the direction 100 of the machine which scores and cuts the retainer. The adhesive strip 92 may be affixed in place prior to cutting the package outline, and the cutting process will then cut both the package and the needle park to their proper dimensions simultaneously. The needle retaining slits 94 are seen to be advantageously parallel to the cut longitudinal edges of the winding panel for further ease in manufacture.

The retainer package of FIG. 11a is assembled as shown in FIG. 11b by winding the suture against the winding panel before inserting the needle in the needle park. The suture holding panels 14 and 16 are folded over the wound suture to hold it in place, and the needle park panel 90 is then folded over the wound suture and the needle 60 is inserted in one of the slits 94 in the foam member 92. As FIG. 11b shows, this process results in the foam member 92 being located angularly with respect to the longitudinal dimension of the retainer package. In this embodiment, the angle is approximately 50°. Unlike the embodiment of FIG. 10c, the needle 60 is located inside the outwardly located upper loop of the suture 62. The folded needle park panel covers the suture, thereby protecting the suture material from damage by the needle.

The fully assembled package is shown in FIG. 11c. It is seen that in this embodiment the foam needle park 92 is entirely protected and covered behind the suture enclosing panel 12 when the package is opened, and that the needle point is also protected behind the enclosing panel and above the needle park 92. The barrel and major portion of the body of the needle 60 are in full view of the user so that the needle may be readily grasped with a forceps for withdrawal of the needle and suture. The loops of suture will smoothly slide out of the retainer package from behind the needle park panel 90 without becoming snagged on the needle park, which is on the reverse side of the panel 90. The corner 99 of the winding panel 10 opposite the score line 98 is seen to be angled to afford ease in grasping the tear flap 23 when the package is to be opened.

When the retainer packages of FIGS. 10c and 11c are to be enclosed in foil-film overwraps or other overwrap packaging, it may be desirable to omit the tear flap 23 altogether. This may be especially desirable when using a clear film overwrap, for the needle and suture are then clearly visible through the overwrap packaging. The user can then clearly see and identify the product before the package is opened.

What is claimed is:

1. An improved retainer for surgical sutures which encloses a surgical suture attached to a surgical needle comprising:
   a panel on which means for holding a surgical needle is to be located, said location including two parallel slots; and
   a foam needle holder, including a central region including a slit for holding a surgical needle, and a pair of outwardly extending insertion tabs for inserting into said parallel slots, said parallel slots being spaced with respect to the dimension of said central region such that said central region of said needle holder assumes an inverted v-shape when said tabs are inserted in said slots.

2. The improved retainer of claim 1, wherein said slots exhibit a given length, and wherein the length of said central region of said needle holder is greater that said length of said slots.

3. The improved retainer of claim 2, wherein the opposite ends of said central length of said needle holder are cut in a v-shape with the apexes of said v-shaped aligned with the center of said central length.

4. An improved retainer for surgical sutures which encloses a surgical suture, said retainer including two outer panels each having a longitudinal dimension and a transverse dimension, said retainer comprising:
   a tear flap located at one end of one of said outer panels, said tear flap including at one corner of said retainer an unattached corner which is to be grasped by a user to open said retainer, a hinged side located on the longitudinal side of said retainer opposite said unattached corner, and a scored line extending transverse said retainer between said unattached corner and said hinged side of said tear flap,
   wherein said scored line is torn open when said tear flap is opened by a user.

5. An improved retainer for surgical sutures which encloses a surgical suture, comprising:
   a suture winding panel having a pair of longitudinal edges and a pair of transverse edges;
   a needle holding means disposed adjacent a first transverse edge of said suture winding panel;
   a suture enclosing panel having a pair of longitudinal edges and a pair of transverse edges, a transverse edge of said suture enclosing panel being foldably connected to a second transverse edge of said suture winding panel; and
   a suture winding insert having a pair of longitudinal edges which are less than the longitudinal length of said suture winding panel and a pair of transverse edges which are substantially equal to the transverse dimension of said suture winding panel,
   wherein, when said suture winding insert is place against said suture winding panel, a wound suture may be located against said insert and a needle attached to said suture may be located in said needle holding means with the point of said needle located between said suture winding panel and said suture winding insert.

6. The improved retainer of claim 5, wherein a portion of said needle holding means is located between said suture winding insert and said suture winding panel.

7. The improved retainer of claim 6, wherein said suture winding insert further includes a flap foldably connected to the transverse edge of said insert opposite the transverse edge which is adjacent said needle holding means, wherein said foldable connection of said flap is aligned with the foldable connection of said suture winding panel and said suture enclosing panel.

* * * * *